US011045551B2

(12) United States Patent
Afinogenova et al.

(10) Patent No.: US 11,045,551 B2
(45) Date of Patent: Jun. 29, 2021

(54) ANTISEPTIC COMPOSITION COMPRISING POLYVINYLPYRROLIDONE AND UNITHIOL AND USE OF THE COMPOSITION (71) Applicant: MEDID INNOVATION DEVELOPMENT LTD, Limassol (CY)

(72) Inventors: Anna Gennadievna Afinogenova, St. Petersburg (RU); Gennady Evgenievich Afinogenov, St. Petersburg (LT); Tamaz Omarovich Manasherov, Moscow (RU); Svetlana Konstantinovna Matelo, Mechnikovo (RU)

(73) Assignee: MEDID INNOVATION DEVELOPMENT LTD, Limassol (CY)

( * ) Notice: Subject to any disclaimer, the term of this patent is extended or adjusted under 35 U.S.C. 154(b) by 22 days.

(21) Appl. No.: 16/480,536

(22) PCT Filed: Dec. 14, 2017

(86) PCT No.: PCT/RU2017/000905
§ 371 (c)(1),
(2) Date: Jul. 24, 2019

(87) PCT Pub. No.: WO2018/156051
PCT Pub. Date: Aug. 30, 2018

(65) Prior Publication Data
US 2019/0381176 A1 Dec. 19, 2019

(30) Foreign Application Priority Data

Feb. 22, 2017 (RU) .......................... RU2017106061

(51) Int. Cl.
| A61K 47/32 | (2006.01) |
| A61P 17/02 | (2006.01) |
| A61P 31/02 | (2006.01) |
| A61K 31/14 | (2006.01) |
| A61K 31/167 | (2006.01) |
| A61K 31/235 | (2006.01) |
| A61K 31/498 | (2006.01) |
| A61K 33/38 | (2006.01) |
| A61K 47/20 | (2006.01) |

(52) U.S. Cl.
CPC .............. *A61K 47/32* (2013.01); *A61K 31/14* (2013.01); *A61K 31/167* (2013.01); *A61K 31/235* (2013.01); *A61K 31/498* (2013.01); *A61K 33/38* (2013.01); *A61K 47/20* (2013.01); *A61P 17/02* (2018.01); *A61P 31/02* (2018.01)

(58) Field of Classification Search
CPC ...... A61K 47/32; A61K 31/14; A61K 31/167; A61K 31/235; A61K 31/498; A61K 33/38; A61K 47/20; A61P 17/02; A61P 31/02
See application file for complete search history.

(56) References Cited

U.S. PATENT DOCUMENTS

| 2,739,922 | A | 3/1956 | Shelanski |
| 3,761,590 | A | 9/1973 | Fox, Jr. |
| 4,614,794 | A | 9/1986 | Easton et al. |
| 6,828,308 | B2 | 12/2004 | Mastradonato et al. |
| 2007/0020213 | A1* | 1/2007 | Tamarkin ............... A61K 8/062 424/70.1 |
| 2016/0346294 | A1* | 12/2016 | Sengupta ............... A61K 47/02 |

FOREIGN PATENT DOCUMENTS

| RU | 2 062 113 C1 | 6/1996 |
| RU | 2 088 234 C1 | 7/1996 |
| RU | 2 175 549 C1 | 11/2001 |
| RU | 2 185 155 C2 | 7/2002 |
| RU | 2 284 824 C1 | 10/2006 |
| RU | 2 545 915 C1 | 4/2015 |
| RU | 2 603 490 C1 | 11/2016 |
| RU | 2 605 343 C1 | 12/2016 |
| WO | 2006/121219 A1 | 11/2006 |
| WO | 2008/027904 A2 | 3/2008 |

OTHER PUBLICATIONS

PVP Polymer Brochure by Asland, 2017.*
International Search Report issued in PCT/RU2017/000905, dated Aug. 30, 2018, pp. 1-5.
Written Opinion issued in PCT/RU2017/000905, dated Aug. 30, 2018, pp. 1-8.
Volf, V. et al., "Combined chelation treatment for polonium after simulated wound contamination in rat" Int. J. Radiat. Biol. (Oct. 1995) pp. 395-404, vol. 68, No. 4.
Tarrand, J.J. et al., "Dimethyl Sulfoxide Enhances Effectiveness of Skin Antiseptics and Reduces Contamination Rates of Blood Cultures" Journal of Clinical Microbiology (Feb. 2012) pp. 1552-1557.
Vidal "Oflomelid" https://www.vidal.ru/drugs/oflomeslid__2017, pp. 1-3, accessed on Jun. 7, 2019.
Darenkov, A. et al., "Ligenten, a combination with anesthetic and antibacterial activity for local application in urologic and gynecologic cases" Elsevier, XP-002779971 (Aug. 1994) pp. 1.

(Continued)

*Primary Examiner* — Blessing M Fubara (74) *Attorney, Agent, or Firm* — Tutunjian & Bitetto, P.C.

(57) ABSTRACT

Polymer-based antiseptic compositions are provided for treating wounds and/or for use in surgical operations, which form a film on the wound surface and have antiseptic, anesthetic and antitoxic effects. The compositions include polyvinylpyrrolidone with a weight average molecular weight in a range of 1,000,000 to 3,000,000 Da, one or more antiseptics, unithiol, dimethylsulfoxide, and one or more anesthetics. In addition, use of the compositions in a wound treatment, as well as methods for treating wounds using the compositions including the step of applying the composition to a wound surface are provided.

17 Claims, 4 Drawing Sheets

(56) References Cited

OTHER PUBLICATIONS

Vidal "Bepanthen plus" https://www.vidal.ru/drugs/bepanthen_%20plus__6796, pp. 1-4, accessed on Jun. 20, 2019.
Blatun L.A. "Local medical treatment of wounds" // Surgery, 2011, No. 4, pp. 1-8, published in Russian language, together with English language abstract.
Nazarenko G.I., Sugurova I.Yu.., Glancev S.P. "Wound. Bandage. Patient.", M.: Medicine, 2002, pp. 174-175, published in Russian language, together with English language abstract.
Volker Bühler, "Kollidon®. Polyvinylpyrrolidone for the pharmaceutical industry", translated from English, ed. by Dr. Alekseeva K.V., BASF, 2001, p. 310, published in Russian language, together with English language abstract.
"Manual on Medical Microbiology. General and Sanitary Microbiology. Volume I", Collective of authors, ed. by Labinskaya A.S., Volina E.G., M.: Publishing House BINOM, 2008, p. 465, published in Russian language, together with English language abstract.
Encyclopedia of medicines "Unithiol" https://www.rlsnet.ru/tn_index_id_5313.htm, pp. 1- 7, accessed on Jun. 21, 2019.

\* cited by examiner

ANTISEPTIC COMPOSITION COMPRISING POLYVINYLPYRROLIDONE AND UNITHIOL AND USE OF THE COMPOSITION

FIELD OF THE INVENTION

The invention pertains to the field of medicine, in particular to the field of wound care and treatment of wound surfaces. Specifically, the invention relates to antiseptic compositions for wound treatment and/or for use in surgical operations, said compositions having antiseptic, anesthetic and antitoxic effects. In addition, the invention relates to use of said compositions for treating wounds and/or during surgical operations, as well as methods for treating wounds using these compositions.

BACKGROUND OF THE INVENTION

Currently, in medical practice, various compositions are widely used for the wound treatment, said compositions being designed to accelerate healing processes, prevent infection of the wound by microorganisms and to physically protect the wound surface from the environment.

Depending on the location of the wound, its contamination, the nature of the injury and other factors, the prior art discloses technical means and compositions of various types useful for the wound treatment.

In particular, for treating wounds contaminated by microorganisms, formulations in the form of ointments and solutions are widely used, said formulations being based on synthetic polymers and iodine, having a sufficiently broad spectrum of antimicrobial activity. In particular, formulations based on polyvinylpyrrolidone-iodine complexes are used (see U.S. Pat. No. 2,739,922 A), examples of said formulations include some well-known products such as Betadine and Wocadin. "Stellanin-PEG 3%" ointment comprising 1,3-diethylbenzimidazolium triiodide, low molecular weight polyvinylpyrrolidone (PVP), dimethylsulfoxide, polyethylene oxides 400 and 1500 is also known. The bactericidal effect of this formulation is also caused by the active iodine comprised in the composition (Blatun L. A. "Local medical treatment of wounds"/Surgery, 2011, no. 4, pp. 1-8, published in Russian language). Use of iodine-based compositions is limited due to possible allergic reactions, as well as in the case of hyperthyroidism. In addition, polyvinylpyrrolidone used in the prior art compositions had a relatively low molecular weight.

In the prior art, expensive silver sulfadiazine based ointments are known as well, said ointments being used for treating burn wounds (see U.S. Pat. No. 3,761,590 A). Examples of the formulations based on silver sulfadiazine are Dermazin, Silvadene, Silvederma and Sulfargin. Contraindications to their use are hypersensitivity to sulfanilamide drugs, as well as severe liver and kidney disorders.

In the prior art, a cream Bepanthen-plus is known for the treatment of superficial wounds, which is a homogeneous soft opalescent cream having a white to yellowish color, with a weak characteristic odor. Cream Bepanthen-Plus comprises dexapanthenol and chlorhexidine as active components, as well as auxiliary substances: pantolactone, cetyl alcohol, stearyl alcohol, lanolin, soft white paraffin, liquid paraffin, macrogol stearate and purified water. Cream Bepanthen-plus is not recommended for use in the case of large, deep and heavily contaminated wounds (Electronic reference book of medical formulations "VIDAL", 2016).

In addition, in the prior art, a wide range of film dressings is known comprising antimicrobial agents in their adhesive layer. The films comprising iodine and chlorhexidine are widely used for the protection of skin around surgical wounds and in the places of punctures around the central and peripheral venous catheters.

In particular, the prior art discloses an antiseptic wound healing adhesive comprising antiseptic miramistin, ethyl alcohol and BF-6 polymer (see the abstract of RU 2185155 C2). This adhesive has antibacterial and antifungal action, enhances regenerative processes in the wounds and protects clean wounds from infection. The field of its use is limited to minor epidermal damage (scratches, abrasions), i.e. the wounds that do not penetrate the entire thickness of the dermis. An adhesive with miramistin is not used in the treatment of soft tissue wounds.

The prior art also discloses combined sponge dressings combining the positive effects of proteins and polysaccharides in the treatment of wounds: creating an environment for healing (alginates and chitosans) and for forming a matrix for growth of newly formed granulation tissue (collagen).

For example, Algicol is an original domestic spongy bandage comprising 25% to 75% of cross-linked collagen and 75% to 25% of (calcium) alginate, respectively. In order to ensure the antimicrobial properties of the bandage, it can comprise 0.5% to 5% of potassium furagin. It has been found that an increase in the collagen amount in the complex leads to an increase in its stability and structural strength. Inclusion of antiseptics (furagin and shikonin) and anesthetics (trimecaine) in the bandage provides for the preparation of a biologically active composite spongy bandage. Algicol is well-proven in the treatment of infected and purulent wounds, stimulating the process of granulations formation and maturation and providing a moderate antiseptic effect. Presently, Algicol is not produced anymore.

Fibracol is a lyophilized sponge comprising fibers of cross-linked collagen with an addition of 10% of a mixture of calcium-sodium alginic acid salt, similar to those described in U.S. Pat. No. 4,614,794 A. When applied to a wound, the film quickly becomes wet and is easily modeled, while retaining its structural properties. It requires a secondary and pressure bandage and a retention layer. Fibracol is a foreign analogue of Algicol (see 'Nazarenko G. I., Sugurova I. Yu., Glancev S. P. "Wound. Bandage. Patient.", M.: Medicine, 2002, pp. 174-175', published in Russian language).

In the prior art, the polymer-based ointment Oflomelid is also known (manufactured by OAO «Syntez») intended for topical application (Registration Certificate No. LSR-007163/09 of Jun. 26, 2013). Oflomelid has antibacterial, local anesthetic effects and improves tissue regeneration. The ointment comprises an anesthetic component of lidocaine, an antimicrobial component of ofloxacin (a fluoroquinolone type antibiotic) and a wound healing component of methyluracil, as well as additives: macrogol 1500 (polyethylene oxide 1500, polyethylene glycol with low molecular weight 1500), macrogol 400 (polyethylene oxide 400, polyethylene glycol with low molecular weight 400), propylene glycol, methyl parahydroxybenzoate (Nipagin or methylparaben), propyl parahydroxybenzoate (Nipazol or propylparaben).

Patent RU 2284824 (C1), fully incorporated herein by reference, discloses an antiseptic composition for use in surgery, which is the closest analogue of the claimed invention. The known composition comprises collagen hydrolysate (50.0 to 80.0 wt %), sodium alginate (1.0 to 10.0 wt %), glycerol (1.0 to 3.0 wt %), benzalkonium chloride (Catapol, 0.5 to 1.0 wt %), dioxidine (0.5 to 2.0 wt %), Poviargol (0.5 to 2.0 wt %), methylparaben (Nipagin, 0.002 wt %), propylparaben (Nipazol, 0.002 wt %) and an aqueous solution of sodium hypochlorite (balance). It has been shown that this composition has a significant antimicrobial effect against the causative agents of infectious complications of wounds (staphylococci, streptococci, gram-negative bacteria, spore-forming and non-spore-forming anaerobes, Candida fungi, etc.), anti-inflammatory and wound-healing properties. It provides for aseptic healing conditions, protects the wound from external mechanical influences, contamination and infection. The combined use of antiseptics having different mechanisms of action leads to a significant antimicrobial effect, and the ratio of biopolymer concentrations (that is, collagen and sodium alginate) ensures the ability to control biodegradation of the adhesive, thus providing an acceleration of wound healing as a result. Important disadvantages of the known composition are the following:

the biodegradable composition based on collagen hydrolysates may be ineffective at the prehospital stage due to its rapid biodegradation on the wound surface;

the known composition does not show an antitoxic action for suppressing toxins, emerging from both the damaged tissues and the products of pathogenic microorganisms metabolism;

the known composition does not possess the ability to suppress penetration of microorganisms into soft tissues and into the bloodstream.

In the prior art, it is known that in the case of severe mechanical damage, the negative impact of neural pain impulses, endotoxicosis and other factors inevitably adds to the pathological effect of the hemorrhage, thus always making the condition of the patient with a traumatic shock heavier as compared to the "pure" blood loss of equal volume. With further aggravation of the traumatic shock due to the growing deficit in the oxygen delivery to the tissues, the energy production switches to the anaerobic glycolysis pathway, and the body accumulates acidic products (lactic acid, etc.) and toxic substances of several types: toxic amines (histamine, serotonin, prostaglandin), polypeptides (bradykinin, kallidin), enzymes (lysosomal amines), tissue metabolites (electrolytes, adenyl compounds, ferritin). They all inhibit blood circulation, respiration, contribute to the breakdown of antimicrobial barriers and development of irreversible changes in the cells. Metabolic acidosis develops, which plays an important pathogenetic role in the late period of the traumatic shock (stimulation of adrenal medulla function, electrolyte imbalance, increased intravascular fluid volume). Autocatalytic flooding of the body with toxic substances aggravates the crisis of microcirculation, disrupts functions of a number of organs and systems. At the final stage of the traumatic shock, due to the oxygen deficiency, the endotoxicosis, impaired liver and other organs function, irreversible death of cellular structures ("refractory" shock) develops; death of the patient becomes inevitable.

Despite the large amount of information available in the prior art on various compositions used for wound treatment and/or during surgical operations, there is still a significant demand for new compositions having antiseptic, anesthetic and antitoxic properties in the art.

Therefore, an object of the present invention is to provide novel antiseptic compositions capable of overcoming the disadvantages of the compositions known from the prior art, in particular, are non-biodegradable, exhibit additional antitoxic and anesthetic properties, and have the ability to inhibit penetration of microorganisms into soft tissues and into the bloodstream.

SUMMARY OF THE INVENTION

To solve the above technical problem, the inventors have developed new antiseptic compositions on the basis of a polymer, said compositions being intended for treating wounds and/or for use during surgical operations, capable of forming a film on the wound surface and having an antiseptic, anesthetic, anti-inflammatory, wound-healing, and antitoxic effects, as well as the ability to prevent penetration of microorganisms from the wound in the blood.

The compositions according to the invention comprise polyvinylpyrrolidone with a weight-average molecular weight in the range of 1,000,000 to 3,000,000 Da, one or more antiseptics, unithiol, dimethylsulfoxide, and one or more anesthetics, preferably local anesthetics.

In addition, the invention relates to the compositions according to the invention intended for use in wound treatment.

In addition, the invention relates to use of the compositions according to the invention as an agent for wound treatment.

The present invention also relates to methods for treating wounds using the compositions according to the invention, said method comprising the step of applying the composition according to the invention to a wound surface.

Other aspects of the present invention will be apparent to those skilled in the art from the following description and from the appended claims.

The inventors have surprisingly found that the compositions according to the invention form a film on the wound surface, said film providing an advantageous combination of antiseptic, anesthetic and antitoxic properties, having a significant antimicrobial effect against various pathogens causing infectious wound complications, and is able to prevent the entry of the microorganisms from the wound into the blood.

The compositions according to the invention have a good adhesion to the skin and tissues and provide additional fixation of the dressing on the surface of the skin around the wound.

In particular, an advantageous property of the compositions according to the invention is their ability to exert a significant detoxication effect when applied to the wound surface, which can lead to a significant acceleration of the healing process and an improvement in the general condition of the patient.

DETAILED DESCRIPTION OF THE INVENTION

The term "wound" in the present invention is understood as a trauma of any part of a human or animal body with a violation of the skin and/or mucous membrane integrity. Preferably, in the present invention, the "wound" is meant to represent a damage caused by a physical impact, however, the damage caused by other damaging factors is also included in the meaning of the "wound" in the present invention.

The wounds in the present invention include both accidental wounds (domestic and industrial injuries, injuries from accidents and natural disasters, etc.), and wound that are inflicted deliberately (such as wounds from surgical operations, as a result of fighting and/or unlawful actions of a third party, etc.).

Wounds can be classified as aseptic, i.e. applied in sterile conditions, and infected. Infected wounds can be primarily infected, i.e. caused by a non-sterile object, and infected after the injury occurred (secondary infection).

The term "polyvinylpyrrolidone" or "PVP" in the present invention means a polymer having the formula PVP is widely used in the art as an auxiliary binder in the tablet preparation. In the field of wound treatment, polyvinylpyrrolidone is mainly used in a complex with iodine, which has a direct antiseptic effect. For this purpose, polyvinylpyrrolidone having a Fickentscher constant value (Fickentscher K or K Value is a coefficient describing viscosity of the polymer) of 10 to 60, which roughly corresponds to values of weight-average molecular weight of about 10,000 to about 400,000 Da, is generally used in the prior art. For the purposes of the present invention, PVP with a molecular weight of 1,000,000 to 3,000,000 Da is used.

The term "molecular weight", when it refers to a polymeric substance, means a weight-average molecular weight Mw in the present invention. However, in some cases, this expression can also correspond to the number-average molecular weight Mn.

Unithiol, in the present invention, means sodium salt of 2,3-bis(sulfanyl)propane-1-sulfonic acid (2,3-bis(sulfanyl)propane-1-sulfonic acid may also be referred to as unithiol). Unithiol is known in the prior art as a chelating agent capable of binding via its active sulfhydryl groups to arsenic compounds and salts of heavy metals in blood and tissues, thus inactivating them and facilitating their removal from the body. The antidote and detoxication action of unithiol is ensured by the presence of two sulfhydryl groups (—SH), capable of forming complex bonds, which can form a fairly stable complex with heavy metals, thus having an antidote effect. Use of unithiol as an antidote in arsenic compounds and heavy metal salts poisoning results in binding of these heavy metals in the blood and tissues and in restoration of the function of the affected enzyme systems of the body. The same mechanism of action manifests when treating hepatocerebral dystrophy (Wilson disease) using unithiol, in which case, among other symptoms, there are abnormalities of the copper exchange and copper accumulation in the subcortical nuclei of the brain. Compared with its analogue, dimercaprol or 2,3-bis(sulfanyl)propan-1-ol, unithiol is less toxic, and its good solubility in water makes it more convenient for use and provides for its rapid absorption. Unithiol is included in the list of vital and essential drugs. The main indications for its use are acute and chronic poisoning by organic and inorganic compounds of arsenic, mercury, gold, chromium, cadmium, cobalt, copper, zinc, nickel, bismuth, antimony; intoxication with cardiac glycosides, hepatocerebral dystrophy (Wilson's disease). It is also used to bind products of incomplete oxidation of ethyl alcohol causing hangover. Use of unithiol in acute poisoning does not exclude other therapeutic measures (gastric lavage, inhalation of oxygen, administration of glucose and others). In addition, use of unithiol has been reported in the case of some other poisonings and diseases. There are data on the beneficial effect of unithiol in diabetic polyneuropathies. Perhaps this is due to the fact that patients with diabetes mellitus have a reduced content of sulfhydryl groups in the blood.

In the present invention, the expressions "comprises" and "includes" and their derivatives are used interchangeably and are understood as being non-limiting, i.e. allowing for a presence/use of other components, stages, conditions, etc., in addition to those listed explicitly. On the contrary, the expression "consists of", "is composed of" and their derivatives are intended to mean that the components, stages, conditions and the like listed after that are exhaustive.

In the present invention, when a range of possible values is provided for any value, it is to be understood that the upper and lower limits of the range are also included in the scope of the invention. It should also be understood that all the sub-ranges within the provided ranges are also included in the scope of the present invention as if they were disclosed explicitly. In case several ranges of possible values are provided for any value, all the ranges obtained by combining different endpoints of these ranges are also included in the present invention as if they were disclosed explicitly.

In case any features of the invention are disclosed herein for a single embodiment, the same features may also be used in all other embodiments of the invention, provided it does not contradict the spirit and technical sense of the invention.

With the exception of the experimental part of the description, all numerical values defining any quantities and conditions in the present invention are approximations and should be read as preceded by the word "about", even when said word is not directly mentioned. On the contrary, all numerical values recited in the experimental part of the description are given as precisely as possible. However, it should be understood that any experimentally found value comprises a certain error due to its very nature. Thus, all the numerical values given in the experimental part of the description should be read with taking into account the existence of said experimental error and, at the very least, the number of the available significant digits and standard rounding techniques.

The compositions according to the invention comprise polyvinylpyrrolidone having a molecular weight in the range of 1,000,000 to 3,000,000 Da, one or more antiseptics, unithiol, dimethylsulfoxide and one or more anesthetics, preferably local anesthetics.

Not wishing to be bound by any theory, the inventors believe that polyvinylpyrrolidone with a molecular weight of 1,000,000 to 3,000,000 Da, when used as a base for the wound treatment composition, forms a film on the surface of the skin, prevents contamination of the wound, binds the formed toxins and prevents penetration of microorganisms from the wound surface into tissues and blood vessels. The inventors have surprisingly found that the molecular weight of polyvinylpyrrolidone has a significant effect on the speed and intensity of the wound healing process, when the compositions according to the invention are used. In a preferred embodiment, the molecular weight of the polyvinylpyrrolidone in the compositions according to the invention is about 2,000,000 Da.

The amount of polyvinylpyrrolidone in the compositions according to the invention may vary in a wide range and depends, inter alia, on the required mechanical properties of the film produced on the wound surface, as well as on the amount of other components present in the composition. In some embodiments, the composition according to the invention may comprise about 5 wt % to about 10 wt % of PVP based on the total weight of the composition. In some embodiments, the amount of PVP in the composition according to the invention may be about 6 to about 9.5 wt %, about 7 to about 9 wt %, about 8 to about 9 wt %, preferably about 8.5 to about 9 wt %, based on the total weight of the composition.

The compositions according to the invention also comprise unithiol (sodium 2,3-bis(sulfanyl)propane-1-sulphonate). Not wishing to be bound by any theory, the inventors believe that unithiol, when the composition according to the invention is applied to the wound surface, binds microbial and tissue toxins and thus directly exerts a detoxication effect in the wound. This effect is highly surprising, as there have been no reports on the ability of unithiol to bind microbial and tissue toxins in the prior art. Moreover, nothing has been known on the ability of unithiol to bind microbial and tissue toxins when applied topically on the wound surface. In the present invention, the inventors have shown that use of the claimed compositions for treating wounds results in a significant acceleration of wound healing processes.

The amount of unithiol in the compositions according to the invention may vary depending on the contamination of the wound, the nature of the damage, the intensity of the inflammatory process, and other factors. A person skilled in the art, on the basis of his/her own knowledge, the prior art, and routine experiments, will be able to easily determine the amount of unithiol that should be used in each particular case. In some embodiments, the composition according to the invention may comprise about 0.1 to about 10 wt % of unithiol, based on the total weight of the composition. In some embodiments, the amount of unithiol in the composition according to the invention may be about 0.5 to about 9 wt %, about 1 to about 8 wt %, about 1 to about 7 wt %, about 2 to about 7 wt %, about 3 to about 6 wt %, preferably about 3 to about 5 wt % or about 4 to about 5 wt %, based on the total weight of the composition.

The compositions according to the invention also comprise dimethylsulfoxide. Not wishing to be bound by theory, the inventors believe that dimethylsulfoxide, when used in the compositions according to the invention, contributes to the penetration of the active ingredients of the composition into the skin and soft tissues, thereby providing for an enhancement of efficacy of the active components of the composition.

The amount of dimethylsulphoxide in the compositions according to the invention may vary in a wide range. A person skilled in the art, on the basis of his/her own knowledge, the prior art, and routine experiments, will be able to easily determine the amount of dimethylsulphoxide to be used in each particular case. In some embodiments, the composition according to the invention may comprise about 0.05 to about 5 wt % of dimethylsulfoxide, based on the total weight of the composition. In some embodiments, the amount of dimethylsulphoxide in the composition according to the invention may be about 0.1 to about 4 wt %, about 0.2 to about 3 wt %, about 0.5 to about 2 wt %, about 0.7 to about 1.5 wt %, about 0.8 to about 1.3 wt %, preferably about 1 wt %, based on the total weight of the composition.

As indicated above, the compositions according to the invention comprise one or more antiseptics. It is well known to one of ordinary skill in the art, from the common knowledge and the prior art, what antiseptics can be used in wound treatment compositions and wound dressings. In particular, the choice of antiseptics may depend on the type of suspected infection agents. If it is necessary to obtain a wide spectrum of antimicrobial activity against a wide range of infectious agents, it is preferable to use several antiseptics in the composition according to the invention, said antiseptics having different mechanisms of action, thus resulting in a significant antimicrobial effect against most of the main infectious agents known to cause wound complications (staphylococci, streptococci, gram-negative bacteria, spore-forming and non-spore-forming anaerobes, fungi of the *Candida* genus, etc.). For example, the following antiseptics are illustrative antiseptics suitable for use in the present invention: oxyquinoline derivatives, such as dioxidine (hydroxymethyl quinoxylindioxide); quaternary ammonium compounds, such as miramistin and benzalkonium chloride; silver-based antiseptics, such as poviargol (silver nanoclusters stabilized with low molecular weight polyvinylpyrrolidone, "ARGAKOL. Collected materials on the use of wound coating"! ed. Afinogenov G. E., St. Petersburg, "Borey Art" Publishing House, 2008, p. 30; see also RU 2088234 C1, all published in Russian language); biguanides, such as chlorhexidine, polyhexamethylene-biguanide derivatives; bisphenols, such as triclosan; parabens, such as methylparaben and propylparaben; alcohols such as glycerol; chlorine compounds such as sodium hypochlorite; iodine compounds such as povidone-iodine (iodine complex with polyvinylpyrrolidone) and the like.

The amount of antiseptic(s) used in the compositions according to the invention depends on the antiseptic(s) type, the type of pathogen, the nature of the wound, and other factors. A person skilled in the art, on the basis of his/her own knowledge, the prior art and routine experiments, can easily determine the amount of antiseptic(s) to be used in each particular case. In some embodiments, the amount of antiseptic(s) in the composition according to the invention may be about 0.01 to about 20 wt %, based on the total weight of the composition. In some embodiments, the amount of antiseptic(s) in the composition according to the invention may be about 0.05 to about 15 wt %, about 0.1 to about 12 wt %, about 0.1 to about 10 wt %, about 0.15 to about 10 wt %, about 0.2 to about 9 wt %, about 0.3 to about 8 wt %, about 0.4 to about 7 wt %, about 0.5 to about 6 wt %, about 0.5 to about 5 wt %, about 0.6 to about 5 wt %, about 0.7 to about 4 wt %, about 0.8 to about 3 wt %, or from 1 to about 2 wt %, based on the total weight of the composition.

In one preferred embodiment, the composition according to the invention comprises dioxidine as an antiseptic or one of the antiseptics. The amount of dioxidine in the composition according to the invention can be about 0.1 to about 10 wt %, for example about 0.2 to about 7 wt %, such as about 0.5 to about 5 wt %, such as about 1 to about 4 wt %, such as about 1 to about 3 wt % or about 1.5 to about 2 wt %, based on the total weight of the composition.

In one preferred embodiment, the composition according to the invention comprises poviargol as an antiseptic or one of the antiseptics. The amount of poviargol in the composition according to the invention can be about 0.1 to about 10 wt %, for example about 0.2 to about 7 wt %, such as about 0.5 to about 5 wt %, such as about 1 to about 4 wt %, such as about 1 to about 3 wt %, or about 1.5 to about 2 wt %, based on the total weight of the composition.

In one preferred embodiment, the composition according to the invention comprises benzalkonium chloride as an antiseptic or one of the antiseptics. The amount of benzalkonium chloride in the composition according to the invention may be about 0.01 to about 2 wt %, for example about 0.02 to about 1 wt %, such as about 0.05 to about 0.7 wt %, such as about 0.05 to about 0.5 wt %, such as about 0.07 to about 0.5 wt %, such as about 0.1 to about 0.3 wt %, preferably about 0.15 wt %, based on the total weight of the composition.

In one preferred embodiment, the composition according to the invention comprises methylparaben as an antiseptic or one of the antiseptics. The amount of methylparaben in the composition according to the invention may be about 0.001 to about 2 wt %, for example about 0.01 to about 1 wt %, such as about 0.05 to about 0.5 wt %, such as about 0.05 to about 0.2 wt %, such as about 0.07 to about 0.15 wt %, preferably about 0.1 wt %, based on the total weight of the composition.

In one preferred embodiment, the composition according to the invention comprises propylparaben as an antiseptic or one of the antiseptics. The amount of propylparaben in the composition according to the invention may be about 0.001 to about 2 wt %, for example about 0.005 to about 1 wt %, such as about 0.01 to about 1 wt %, such as about 0.01 to about 0.5 wt %, such as about 0.05% to about 0.1 wt %, based on the total weight of the composition.

In one preferred embodiment according to the invention, the composition according to the invention comprises a combination of dioxidine, poviargol, benzalkonium chloride, methylparaben and propylparaben, taken in the amounts indicated above, as an antiseptic.

The composition according to the invention may additionally comprise one or more anesthetics to reduce the pain syndrome threshold and improve microcirculation in the blood vessels. An addition of anesthetic(s) into the composition according to the invention can prevent the onset of a traumatic shock, subsequent circulatory disorders in the area of injury, which, in their turn, may lead to additional intoxication due to the production of toxins by damaged tissues and additional worsening of the condition of the affected human or animal. One skilled in the art is well aware of anesthetics that can be used in wound treatment compositions and dressings. For example, lidocaine, trimekain, tetracaine, novocaine, etc, may be listed as illustrative examples of the anesthetics suitable for use in the compositions according to the invention. In one embodiment, a preferred anesthetic suitable for use in the compositions according to the invention is lidocaine.

The amount of anesthetic(s) in the compositions according to the invention may vary within a wide range according to the anesthetic type, and the nature and the contamination of the wound, the intensity of inflammation and other factors. A person skilled in the art, on the basis of his/her own knowledge, the prior art and routine experiments, can easily determine the amount of anesthetic(s) to be used in each particular case. In some embodiments, the amount of anesthetic(s) in the composition according to the invention may be about 0.01 to about 10 wt %, based on the total weight of the composition. In some embodiments, the amount of anesthetic(s) in the composition according to the invention may be about 0.05 to about 8 wt %, about 0.1 to about 7 wt %, about 0.5 to about 6 wt %, about 0.5 to about 5 wt %, about 1 to about 5 wt %, about 1.5 to about 4 wt %, or about 2 to about 3 wt %, based on the total weight of the composition.

The compositions according to the invention may also comprise other auxiliary components selected from those conventionally used in the art. Such auxiliary components may be, for example, additional pharmaceutical agents, wetting agents, surfactants, viscosity modifiers, stabilizers, substances promoting tissue regeneration and growth, cytokines, vitamin K, fibrinogen, thrombin, factor VII, factor VIII, colorants, flavoring agents and the like.

Suitable amounts of such auxiliary components can be determined by a person skilled in the art based on general knowledge and the prior art. For example, the auxiliary components may be present in the composition according to the invention in an amount of 20 wt % or less, for example 10 wt % or less, 5 wt % or less, 2.5 wt % or less, 2 wt % or less, 1.5 wt % or less, 1 wt % or less, 0.5 wt % or less, or even 0.1 wt % or less.

In addition, the compositions according to the invention may comprise a suitable carrier. The carrier in the compositions according to the invention is selected from pharmaceutically acceptable carriers conventionally used in the art for the preparation of compositions and dressings for wound treatment. In some embodiments, the carrier in the composition according to the invention may be an aqueous carrier, preferably water. The amount of the carrier is selected based on the practical usability reasoning. In particular, viscosity of PVP aqueous solutions with concentrations above 10% strongly depends on temperature. The greater the concentration of the aqueous solution of PVP, the faster its viscosity decreases with increasing temperature (Volker Buhler, "Kollidon®. Polyvinylpyrrolidone for the pharmaceutical industry", translated from English, ed. by Dr. Alekseeva K. V., BASF, 2001, p. 310, published in Russian language). This effect can be expected in the patients with various injuries and purulent-inflammatory diseases, who have an increased body temperature as a result of the injury. At the same time, when using much lower concentrations, the PVP solution may have insufficient viscosity to be a base for a hydrogel. In this regard, in order to prepare the compositions according to the invention, an aqueous solution of PVP with a concentration of about 10 wt % is preferably used as a base.

A composition according to the invention can be prepared by mixing the ingredients of the composition. In a preferred embodiment, the compositions according to the invention are in the form of an amorphous gel. The order of the components addition is not limited in any particular way and can be selected by a skilled person based on the practical usability reasoning.

The prepared composition according to the invention may be applied to a wound surface. According to the present invention, the composition may be applied in one or more layers using methods conventionally used in the art. If necessary, the conventional means used in the art for this purpose may be used to apply the composition, such as, for example, sterile wipes, syringes, spatulas, and the like.

The application of the composition may be preceded by a primary wound treatment, which is aimed at stopping the bleeding, cleaning the wound, infection prevention, and the like.

In addition, the composition according to the invention may be applied to the wound during or after the completion of a surgical operation, for example immediately before or after suturing the wound.

If necessary, the applied composition may be additionally fixed using conventional means used in the art for this purpose, such as, for example, a sterile gauze dressing and the like.

The invention will now be illustrated using specific exemplary embodiments. These examples are not intended to limit the scope of the invention and are intended solely for illustrating the main principles of the present invention. Specific features disclosed in the examples are not to be construed as limiting the scope of the invention by these specific features. On the contrary, it should be appreciated by one skilled in the art that the specific features of the invention illustrated in the examples are just several of the preferred and yet simple and clear embodiments of the general principles on which the claimed invention is based, said embodiments intended to help a skilled person in understanding the scope of the claimed invention in its entirety as defined in the appended claims.

Example 1

PVP was obtained from commercial sources.

To prepare compositions based on PVP with a molecular weight of 1,000,000 Da according to the invention, an aqueous PVP solution Kollidon 90 F manufactured by BASF (Germany) was used. PVP named Kollidon 90 F is a pharmaceutically pure, free-flowing white or yellowish-white powder with particles of different sizes, with a specific odor. The weight average molecular mass of Kollidon 90 F PVP is 1,000,000-1,500,000 Da (Volker Bühler, "Kollidon®. Polyvinylpyrrolidone for the pharmaceutical industry", translated from English, ed. by Dr. Alekseeva K. V., BASF, 2001, p. 310, published in Russian language)). An aqueous solution of Kollidon 90 F PVP was prepared by dissolving 10 g of the PVP powder in 100 ml of sterile distilled water.

To obtain compositions based on PVP with a molecular weight of 500,000; 2,000,000 and 3,000,000 Da, a 10% aqueous solution of PVP produced by OOO Orgpolymersynthesis (St. Petersburg) was used. 10% aqueous solution of PVP, supplied by OOO Orgpolymersynthesis, is a sterile viscous transparent slightly colored liquid with a specific faint odor (http://www.orgpol.ru/). The weight average molecular weight of the PVP produced by OOO Orgpolymersynthesis in the form of aqueous solutions was from 500,000 to 3,000,000 Da.

Antiseptic compositions were prepared, wherein polyvinylpyrrolidone with a molecular weight of 500,000 Da (Sample 1), a molecular weight of 1,000,000 Da (Sample 2), a molecular weight of 2,000,000 Da (Sample 3), was used as a base; a composition according to RU 2284824 (Control 1) and a composition according to the present invention on the base of polyvinylpyrrolidone with a molecular weight of 2,000,000, but without unithiol (Control 2), were prepared as a comparative formulation.

The resulting compositions were as illustrated in Tables 1-5.

TABLE 1

Composition based on PVP with Mw 500,000 Da, Sample 1.

| Ingredients | Content, wt % |
|---|---|
| Aqueous solution of PVP with a molecular weight of 500,000 Da | 87.7 |
| Unithiol | 5.0 |
| Poviargol | 2.0 |
| Dioxidine | 2.0 |
| Lidocaine | 2.0 |
| Dimethylsulfoxide | 1.0 |
| Benzalkonium chloride 100% | 0.15 |
| Methylparaben | 0.1 |
| Propylparaben | 0.05 |

TABLE 2

Composition according to the invention based on PVP with Mw 1,000,000 Da, Sample 2.

| Ingredients | Content, wt % |
|---|---|
| Aqueous solution of PVP with a molecular weight of 1000000 Da | 87.7 |
| Unithiol | 5.0 |
| Poviargol | 2.0 |
| Dioxidine | 2.0 |
| Lidocaine | 2.0 |
| Dimethylsulfoxide | 1.0 |
| Benzalkonium chloride 100% | 0.15 |
| Methylparaben | 0.1 |
| Propylparaben | 0.05 |

TABLE 3

Composition according to the invention based on PVP with Mw 2,000,000 Da, Sample 3.

| Ingredients | Content, wt % |
|---|---|
| Aqueous solution of PVP with a molecular weight of 2,000,000 Da | 87.7 |

TABLE 3-continued

Composition according to the invention based on PVP with Mw 2,000,000 Da, Sample 3.

| Ingredients | Content, wt % |
| --- | --- |
| Unithiol | 5.0 |
| Poviargol | 2.0 |
| Dioxidine | 2.0 |
| Lidocaine | 2.0 |
| Dimethylsulfoxide | 1.0 |
| Benzalkonium chloride 100% | 0.15 |
| Methylparaben | 0.1 |
| Propylparaben | 0.05 |

TABLE 4

Composition according to RU 2284824, Control 1.

| Ingredients | Content, wt % |
| --- | --- |
| Hydrolysate of collagen "Belkozin" type A (powder, 100%) | 50 |
| Sodium alginate | 4 |
| Benzalkonium chloride 100% | 0.15 |
| Poviargol | 2 |
| Dioxidine | 2 |
| Glycerol | 2.5 |
| Methylparaben | 0.1 |
| Propylparaben | 0.05 |
| Aqueous solution of sodium hypochlorite | Up to 100 |

TABLE 5

Composition based on PVP with Mw 2.000,000 Da without unithiol, Control 2.

| Ingredients | Content, wt % |
| --- | --- |
| Aqueous solution of PVP with a molecular weight of 2,000,000 Da | 92.7 |
| Poviargol | 2.0 |
| Dioxidine | 2.0 |
| Lidocaine | 2.0 |
| Dimethylsulfoxide | 1.0 |
| Benzalkonium chloride 100% | 0.15 |
| Methyl paraben | 0.1 |
| Propyl paraben | 0.05 |

The compositions were prepared by a simple mixing of the ingredients listed in Tables 1-5. The resulting compositions were in the form of an amorphous gel. The compositions were characterized by a good adhesion to the skin and tissues and ensured a fixation of dressings on the surface of the skin around the wound.

Example 2

Experiments were conducted to evaluate the antitoxic activity of the composition according to the invention on a dermonecrosis model in rabbits. In the experiment, rabbits of the Chinchilla breed weighing 3.0-3.5 kg were used.

The studies were carried out using the compositions obtained in Example 1 (Samples 1-3, Control 1 and Control 2). An additional control was a group of animals treated with a known polymer-based ointment "Oflomelid" (Control 3), and a group of animals that did not receive any therapeutic compositions (Control 4).

"Oflomelid" ointment was obtained from a commercial source and used "as is".

In control 4, the animals (4 rabbits) were injected intradermally with 0.1 ml of Staphylococcus toxin (supernatant after the centrifugation and filtration of the daily broth culture of *S. aureus* 209 P "Oxford") for the test for dermonecrosis ("Manual on Medical Microbiology. General and Sanitary Microbiology. Volume I", Collective of authors, ed. by Labinskaya A. S., Volina E. G., M.: Publishing House BINOM, 2008, p. 465, published in Russian language).

In Control 1, Control 2, Control 3, and in Samples 1-3 (4 rabbits in each group), the animals were injected intradermally with 0.2 ml of a 1:1 mixture of Staphylococcus toxin (0.1 ml) and a corresponding therapeutic composition (0.1 ml) obtained according to Example 1 or, in the case of "Oflomelide", obtained from a commercial source.

After 48 hours, the animals were withdrawn from the experiment, and a histological examination of the skin was performed in the area affected by the Staphylococcus toxin.

A specimen of a skin flap coated with epidermis with significant dystrophic changes in the form of a weak coloration and vacuolization of cells of the spinous layer was obtained in Control 4 (FIG. 1) using the toxin of the test strain of *Staphylococcus aureus*. Dermis was swollen. In its depth, there was a large site of inflammation as represented by a dense infiltration of necrotic tissue by leukocytes, in most of which the nuclei were sequestered. Among them, plasmocytes and macrophages (1) were scattered. The site was delimited by a layer of young edematous granulation tissue with single leucocytes in the depth (2).

Figure 1:
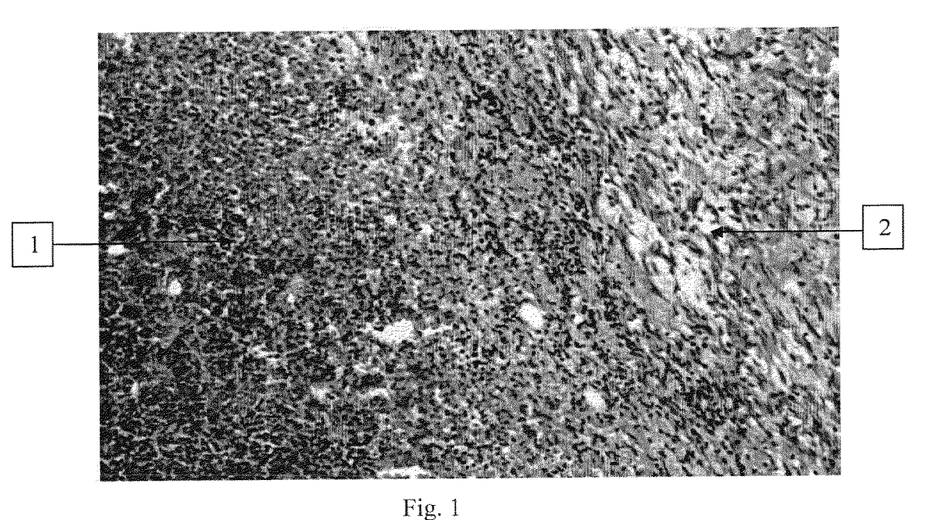
FIG. 1 illustrates a specimen of a skin fragment obtained during a control experiment 48 hours after the intradermal administration of S. aureus toxin for further assessment of the antitoxic activity of various compositions in a dermonecrosis model in rabbits. The staining was carried by hematoxylin and eosin, magnification of 200 times. In this control experiment, no antiseptic compositions were used (Control 4).

Thus, the description of the presented skin flap product testifies to the presence of an acute purulent-necrotic inflammation with a weak delimitation from the surrounding tissue by young granulations and signs of dystrophy, edema and necrosis.

Figure 2:
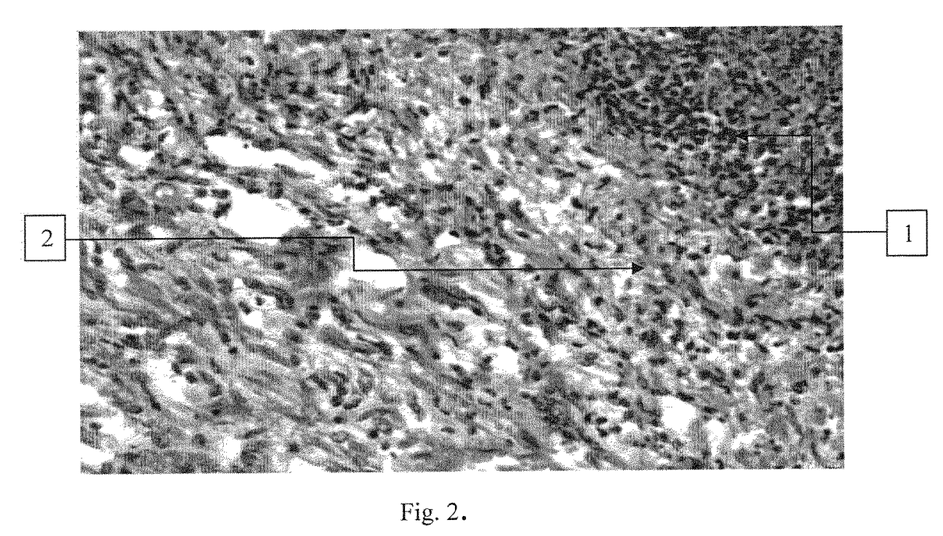
FIG. 2 illustrates a specimen of a skin fragment obtained from a control experiment for assessment of the antitoxic activity in the dermonecrosis model in rabbits 48 hours after the intradermal administration of a mixture of S. aureus toxin and a composition according to RU 2284824, 1:1 (Control 1). The staining was carried by hematoxylin and eosin, magnification of 400 times.

In Control 1 (FIG. 2) using a mixture of *Staphylococcus aureus* toxin and the composition according to document RU 2284824, a skin fragment specimen was obtained where a necrosis site (1) was present, there was a significant inflammatory site with a dense leukocyte infiltration (2).

Figure 3:
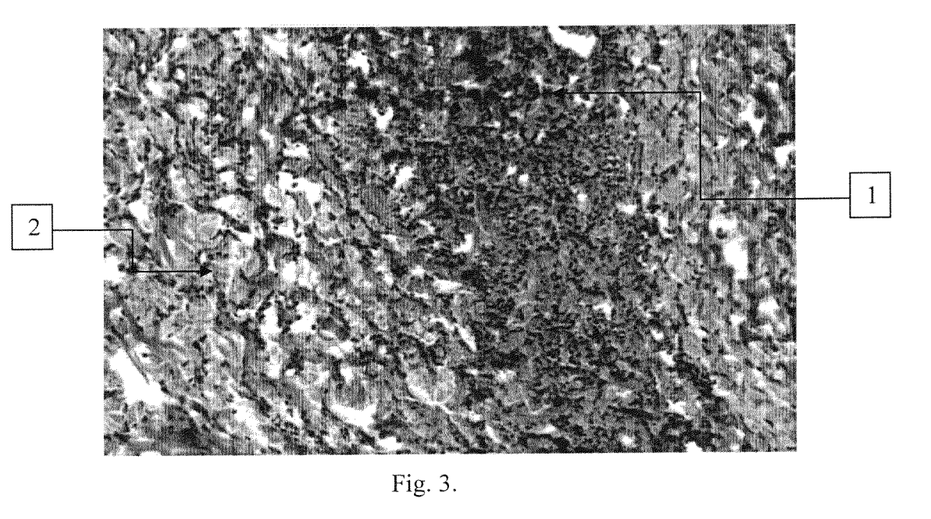
FIG. 3 illustrates a specimen of a skin fragment obtained in a control experiment for assessment of the antitoxic activity of compositions in the dermonecrosis model in rabbits 48 hours after the intradermal administration of a mixture of *S. aureus* toxin and a composition based on PVP with a molecular weight of 2,000,000 Da without unithiol, 1:1 (Control 2). The staining was carried by hematoxylin and eosin, magnification of 200 times.

In Control 2 (FIG. 3) using a mixture of *Staphylococcus aureus* toxin and the composition of the present invention based on a polyvinylpyrrolidone with a molecular weight of 2,000,000 Da, but without unithiol, a skin fragment specimen was obtained where a small site of necrosis (1) was present, said site being localized and bordered by areas of growing and maturing fibrous-granulation tissue with a small infiltration by leukocytes (2).

Figure 4:
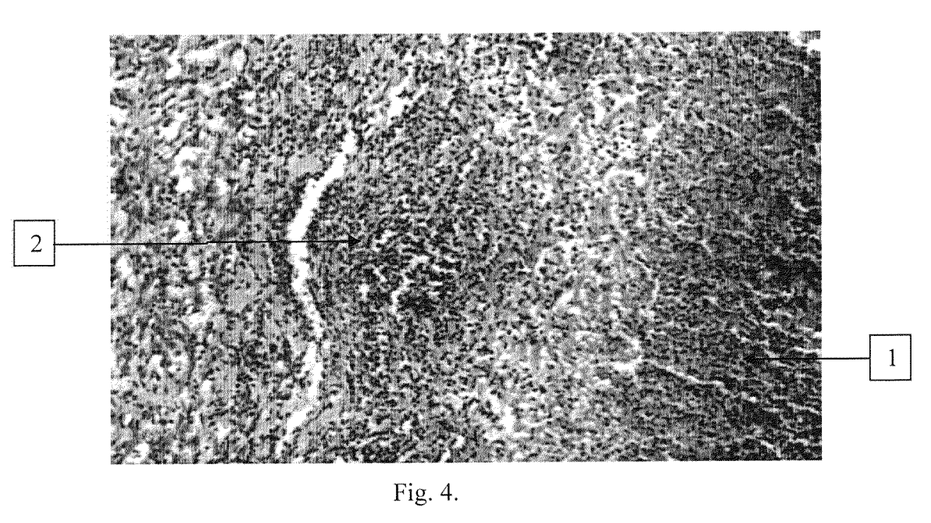
FIG. 4 illustrates a specimen of a skin fragment obtained during a control experiment for assessment of the antitoxic activity in the dermonecrosis model in rabbits 48 hours after the intradermal administration of a mixture of *S. aureus* toxin and "Oflomelid" ointment, 1:1 (Control 3). The staining was carried by hematoxylin and eosin, magnification of 200 times.

In Control 3 (FIG. 4) using a mixture of *Staphylococcus aureus* and "Oflomelid" ointment, a skin fragment specimen was obtained, where a small site of necrosis (1) was present, as well as a significant inflammatory site with a dense leukocyte infiltration (2).

Figure 5:
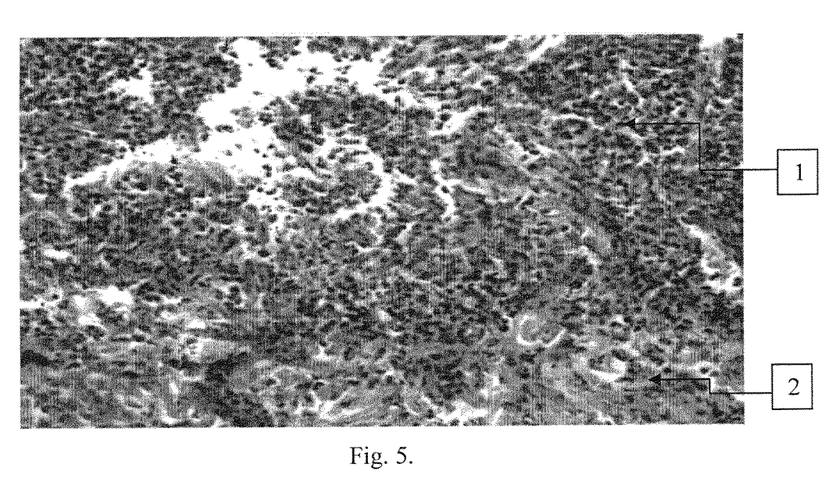
FIG. 5 illustrates a specimen of a skin fragment obtained from an experiment for assessment of the antitoxic activity in the dermonecrosis model in rabbits at 48 hours after intradermal administration of a mixture of *S. aureus* toxin and a composition according to the invention based on PVP with a molecular weight of 500,000 Da, 1:1 (Sample 1). The staining was carried by hematoxylin and eosin, magnification of 400 times.

In experiment 1 (FIG. 5) using a mixture of *Staphylococcus aureus* toxin and Sample 1, a skin fragment specimen was prepared, where a significant inflammatory site with a dense leukocyte infiltration (1) was present in the dermal depth. On the border with the adjacent muscle, a small area of growth of maturing fibrous-granulation tissue with pronounced leukocyte infiltration (2) was located.

Figure 6:
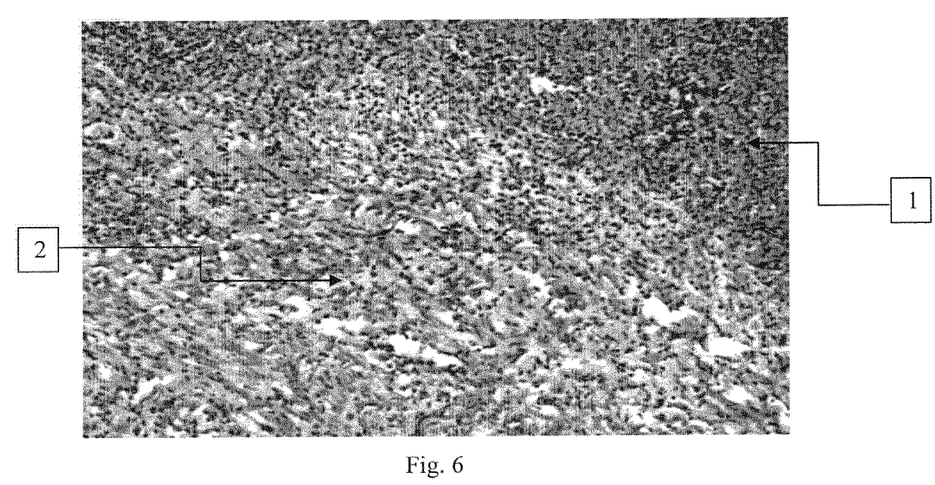
FIG. 6 illustrates a specimen of a skin fragment obtained from an experiment for assessment of the antitoxic activity in the dermonecrosis model in rabbits 48 hours after the intradermal administration of a mixture of *S. aureus* toxin and a composition according to the invention based on PVP with a molecular weight of 1,000,000 Da, 1:1 (Sample 2). The staining was carried by hematoxylin and eosin, magnification of 200 times.

In experiment 2 (FIG. 6) using a mixture of *Staphylococcus aureus* toxin and Sample 2, a skin fragment specimen was prepared, where a small inflammation site with a dense leukocyte infiltration (1) was present in the dermis. On the border with the adjacent muscle, a small area of growth of maturing fibrous-granulation tissue with a small leukocyte infiltration (2) was located.

Figure 7:
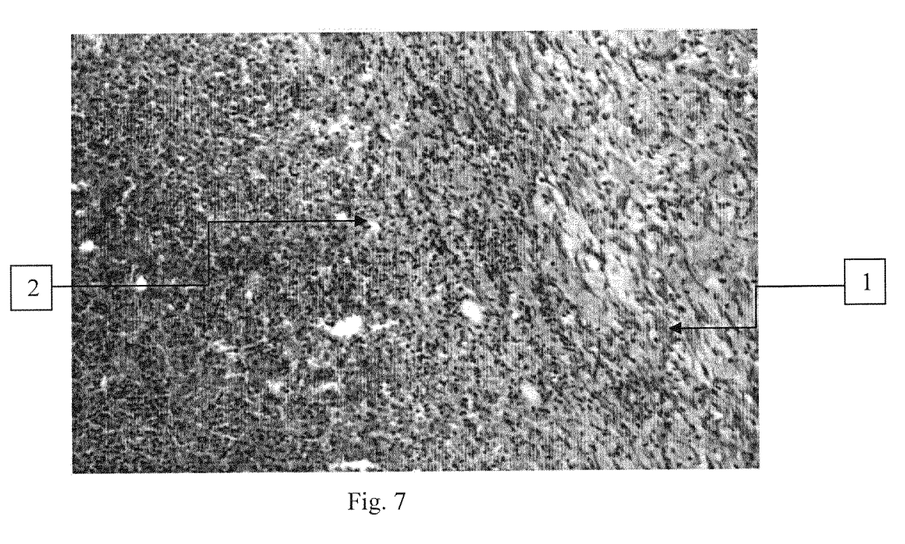
FIG. 7 illustrates a specimen of a skin fragment obtained in an experiment for assessment of the antitoxic activity in the dermonecrosis model in rabbits 48 hours after the intradermal administration of a mixture of *S. aureus* toxin and a composition according to the invention based on PVP with a molecular weight of 2,000,000 Da, 1:1 (Sample 3). The staining was carried by hematoxylin and eosin, magnification of 200 times.

In experiment 3 (FIG. 7) using a mixture of *Staphylococcus aureus* toxin and Sample 3, a specimen of a skin fragment coated with a normal epidermis was obtained. In the thickness of the dermis there are small foci of perivascular lymphocytic infiltration (1). On the border with the adjacent muscle, a site of growth of maturing fibrous-granulation tissue with scattered small accumulations of macrophages and plasmocytes in the depth (2) was located.

Thus, the experiments on the dermonecrosis model in rabbits showed that the prior art composition corresponding to RU 2284824 and sample 1 of the composition based on polyvinylpyrrolidone with a molecular weight of 500,000 Da did not exhibit an antitoxic effect. On the histological skin preparations, there was a site of necrosis and significant inflammation.

Polymer-based ointment "Oflomelid" also had no antitoxic effect. The presence of a site of necrosis and significant inflammation were noted on the corresponding histological skin specimen.

A sample of the composition on the base of polyvinylpyrrolidone with a molecular weight of 2,000,000 Da without unithiol has the ability to partially bind the toxin and localize the inflammation, but on the histological skin specimen, there was a necrotizing site with a small infiltration of lymphocytes.

Sample 2 of the composition according to the invention based on polyvinylpyrrolidone with a molecular weight of 1,000,000 Da with unithiol showed an antitoxic effect, although a small inflammation focus was still noted on the histological skin specimen.

Sample 3 of the composition according to the invention based on polyvinylpyrrolidone with a molecular weight of 2,000,000 Da with unithiol had a significant antitoxic effect. On the histological skin specimen, a lack of necrosis site and a small area of inflammation were observed, sections of growing granulation tissue prevailed on the section.

Example 3

Experiments were conducted to evaluate the ability of the compositions according to the invention to prevent the penetration of opportunistic microorganisms from the wound into the blood, on a dermonecrosis model in rabbits. In the experiment, rabbits of the Chinchilla breed weighing 3.0-3.5 kg were used.

The studies were carried out using the compositions obtained in Example 1 (Samples 1-3, Control 1 and Control 2). An additional control was a group of animals that did not receive any therapeutic compositions (Control 4).

In control 4, the animals (4 rabbits) were injected intradermally with a suspension of daily broth culture of *S. aureus* 209 P Oxford at a dose of $1 \times 10^9$ CFU/ml in physiological saline ("Manual on Medical Microbiology, General and Sanitary Microbiology. Volume I", Collective of authors, ed. by Labinskaya A. S., Volina E. G., M.: Publishing house BINOM, 2008, p. 465, published in Russian language).

In Control 1, Control 2 and in Samples 1-3 (4 rabbits in each group), the animals were intradermally injected with 0.2 ml of mixture of a daily suspension of *S. aureus* 209 P Oxford broth culture at a dose of $1 \times 10^9$ CFU/ml and a corresponding treatment composition in the ratio 1:1 (Control 2, Control 3, Sample 1, Sample 2, Sample 3).

After 6 hours, 24 hours and 48 hours after the culture injection, blood was collected from the ear vein from all the experimental animals, and microbiological analysis of the blood cultures was performed to reveal the growth of the test strain of *Staphylococcus aureus*. The cultures were carried out in vials for aerobic bacteria on a microbiological analyzer BacT/Alert from bioMerieux, France. *Staphylococcus aureus* that grown in the vials was identified with the bacteriological analyzer Vitek2 from bioMerieux, France.

The results of the evaluation of the ability of the tested compositions to localize infection in the wound are provided in Table 6.

TABLE 6

Effect of the test compositions on the growth of *Staphylococcus aureus* in the blood of experimental animals after intradermal administration.

| Composition | Absence (−) or presence (+) of growth of the test strain *S. aureus* 209 P "Oxford" in the blood of rabbits | | |
| --- | --- | --- | --- |
| | After 6 hours | After 24 hours | After 48 hours |
| Control 4 (saline solution) | + | + | + |
| Control 1 (RU 2284824) | + | + | − |
| Control 2.(PVP with Mw 2,000,000 Da without unithiol) | + | + | − |
| Sample 1 (PVP with Mw 500,000 Da) | + | + | − |
| Sample 2 (PVP with Mw 1,000,000 Da) | + | − | − |
| Sample 3 (PVP with Mw 2,000,000 Da) | − | − | − |

As can be seen from the data in Table 6, after the intradermal administration of the test strain of *Staphylococcus aureus* in saline and in the composition corresponding to RU 2284824, the growth of *Staphylococcus aureus* in the blood was observed after 6, 12 and 48 hours.

During the administration of the test strain with the composition on the base of PVP with Mw 2,000,000 without unithiol or with the composition on the base of PVP with Mw 500,000 with unithiol, the growth of staphylococcus in the blood was observed at 6 and 24 hours, but the growth of the test strain was not observed after 48 hours.

When the test strain was administered along with the composition on the base of PVP with Mw 1,000,000 with unithiol, the microbial growth in the blood was observed after 6 hours, but the growth of test strain was not observed after 24 and 48 hours.

When the test strain was administered along with the composition on the base of PVP with Mw 2,000,000 with unithiol, the absence of growth of the test culture at all observation times was noted.

Further increase of the molecular weight of polyvinylpyrrolidone to 3,000,000 did not improve the results of the compositions according to the invention. Given that the supply of PVP with molecular masses above 2,000,000-3,000,000 Da in the market is severely limited, the use of PVP

Example 4

Experiments were conducted to assess the effect of the molecular weight of polyvinylpyrrolidone on ability of the compositions according to the invention to localize infection in the wound and to prevent the entry of microorganisms from the wound into the blood. In the experiment, rabbits of the Chinchilla breed weighing 3.0-3.5 kg were used. The daily culture of *Staphylococcus aureus* 209 P Oxford was used as the infectious agent. The studies were carried out with two similar compositions, in which polyvinylpyrrolidone with a molecular weight of 500,000 Da (hereinafter PVP-500) and polyvinylpyrrolidone with a molecular weight of 2,000,000 Da (hereinafter referred to as PVP-2000) were used as the compositions base.

All manipulations were performed under intravenous thiopental anesthesia. In the first test group (4 rabbits), in aseptic conditions, the diaphysis of the tibia was exposed from the longitudinal section, 2 holes 1.0 mm in diameter were drilled at a distance of 1.0 cm in the cortical layer. The holes were filled with 0.5 ml of staphylococcal inoculum with a density of $2 \times 10^8$ CFU/ml, then 0.1 ml of a composition according to the invention based on PVP-2000 was introduced thereto. Then, as the soft tissues were sutured after the operation, the PVP-2000 composition was injected into the intermuscular spaces surrounding the bone with a syringe.

In the second test group (4 rabbits), the studies were carried out in a similar manner using the PVP-500 based composition.

Every day, blood was taken once a day to analyze the presence of positive blood culture. The animals were withdrawn from the experiment on the 7th day after the operation, and the level of microbial contamination of wounds in CFU/cm$^2$ was compared with the initial one ("Manual on Medical Microbiology. General and Sanitary Microbiology. Volume I", ed. by Labinskaya A. S., Volina E. G., M.: Publishing House BINOM, 2008, p. 1080, published in Russian language; said document being incorporated herein by reference in the cited scope).

The results of the observations are provided in Table 7.

The composition based on polyvinylpyrrolidone with a molecular weight of 500,000 Da was not able to completely prevent the penetration of microorganisms from the wound into the blood during the first 3 days after the operation, but after the first three days, no penetration of microorganisms from the wound into the blood was observed. At the same time, according to the results of the experiment, the composition exhibited an antimicrobial effect up to a level of contamination of $10^4$ CFU/cm$^2$ on day 7 after the operation.

The composition based on polyvinylpyrrolidone with a molecular weight of 2,000,000 Da prevented the entry of microorganisms from the wound into the blood during the entire observation period. At the same time, according to the results of the experiment, the composition exhibited an antimicrobial effect up to a level of contamination of $10^3$ CFU/cm$^2$ on day 7 after the operation.

Example 5

Experiments were conducted to evaluate the antimicrobial activity of the composition according to the invention based on polyvinylpyrrolidone with a molecular weight of 2,000,000 Da (Sample 3 from Example 1) and comparing this activity with the activity of "Oflomelid" ointment. The studies were carried out with respect to both ofloxacin-sensitive and ofloxacin-resistant microorganisms by the standard method of diffusion into agar. The results were evaluated by the growth inhibition zone of the test microbe (in mm). The results are shown in Table 8.

TABLE 8

Comparative evaluation of the antimicrobial activity of "Oflomelide" and the composition according to the invention (Sample 3, PVP with Mw 2,000,000 Da) with respect to the ofloxacin-sensitive and ofloxacin-resistant microorganisms.

| Test-strain | Zone of growth retardation of the test strain, mm (exposure of 24 hours at 37° C.) | |
|---|---|---|
| | Oflomelid | Sample 3 |
| Ofloxacin-sensitive reference strains | | |
| *Staphylococcus aureus* 209P Oxford | 22.7 ± 0.3 | 29.7 ± 0.3 |
| *Klebsiella pneumoniae* ATCC 70603 | 22.3 ± 0.3 | 28.3 ± 0.3 |

TABLE 7

Evaluation of the influence of the molecular weight of polyvinylpyrrolidone on ability of the compositions according to the invention to prevent the penetration of microorganisms from the wound into the blood and to reduce the level of microbial contamination of the wound.

| Preparation | Rabbit No. | Growth of *S. aureus* 209P "Oxford" in blood per day after surgery: | | | | | | | Level of microbial contamination in the wound on day 7 after operation, CFU/cm$^2$ |
|---|---|---|---|---|---|---|---|---|---|
| | | 1 | 2 | 3 | 4 | 5 | 6 | 7 | |
| Antiseptic gel based on PVP-500 | 1 | + | + | + | − | − | − | − | $10^4$ |
| | 2 | + | + | + | − | − | − | − | $10^4$ |
| | 3 | + | + | + | − | − | − | − | $10^4$ |
| | 4 | + | + | + | − | − | − | − | $10^4$ |
| Antiseptic gel based on PVP-2000 | 1 | − | − | − | − | − | − | − | $10^3$ |
| | 2 | − | − | − | − | − | − | − | $10^3$ |
| | 3 | − | − | − | − | − | − | − | $10^3$ |
| | 4 | − | − | − | − | − | − | − | $10^3$ |

Note:
"+" - presence of growth of the test strain; "−" - no growth of the test strain.

TABLE 8-continued

Comparative evaluation of the antimicrobial activity of "Oflomelide" and the composition according to the invention (Sample 3, PVP with Mw 2,000,000 Da) with respect to the ofloxacin-sensitive and ofloxacin-resistant microorganisms.

| Test-strain | Zone of growth retardation of the test strain, mm (exposure of 24 hours at 37° C.) | |
|---|---|---|
| | Oflomelid | Sample 3 |
| Pseudomonas aeruginosa ATCC 27853 | 23.0 ± 0.7 | 30.3 ± 0.3 |
| Acinetobacter baumannii ATCC BAA-747 | 22.3 ± 0.3 | 28.3 ± 0.3 |
| Ofloxacin-resistant clinical strains | | |
| Staphylococcus epidermidis 66.01.14 | 15.7 ± 0.3 * | 29.3 ± 0.3 ** |
| Klebsiella pneumoniae 4058/13 | 14.3 ± 0.3 * | 28.0 ± 0.7 ** |
| Pseudomonas aeruginosa 532/14 | 13.7 ± 0.3 * | 28.7 ± 0.3 ** |
| Acinetobacter baumannii 346/14 | 12.7 ± 0.3 * | 27.3 ± 0.3 ** |

Note:
* the differences in the antimicrobial activity of Oflomelid against sensitive and resistant bacteria are significant ($P < 0.05$);
** the differences in the antimicrobial activity of the composition according to the invention with respect to sensitive and resistant bacteria are not significant ($P > 0.05$);
*** differences in the antimicrobial activity between Oflomelid and Sample 3 are significant ($P < 0.05$) for both sensitive and resistant bacteria.

As can be seen from the data in Table 3, the "Oflomelid" ointment possessed antimicrobial activity against ofloxacin-sensitive reference strains, but had a significantly reduced activity against the ofloxacin-resistant clinical isolates of microorganisms below the standard sensitivity level (according to EUCAST-2015).

The antimicrobial activity of the composition according to the invention based on PVP with a molecular weight of 2,000,000 Da was significantly higher than that of "Oflomelide", both against the ofloxacin-sensitive and the ofloxacin-resistant clinical strains of microorganisms.

Similar experiments were carried out with samples of compositions according to the invention based on PVP with a molecular weight of 1,000,000 Da and based on PVP with a molecular weight of 3,000,000 Da, in which the same results were obtained as for the composition based on PVP with a molecular weight of 2,000,000 Da.

In general, the conducted experiments show that the antiseptic compositions according to the invention have a significant antiseptic and antitoxic effect, and are also capable of preventing the penetration of microorganisms from the wound into the blood and tissues. The compositions according to the invention advantageously differ both from the known biodegradable compositions based on collagen hydrolysates and from known compositions based on synthetic polymers. It has been found that the use of the compositions according to the invention results in a decrease in microbial contamination of the wound, acceleration of the healing processes and the prevention of the spread of microorganisms into the patient's tissues and blood.

The invention claimed is:

1. An antiseptic composition, comprising one or more antiseptics, from 5 to 10 wt % polyvinylpyrrolidone (PVP) having a molecular weight in the range of 1,000,000 to 3,000,000 Da, unithiol, dimethylsulfoxide, and one or more anesthetics, wherein the one or more antiseptics includes a combination of dioxidine, poviargol, benzalkonium chloride, methylparaben and propylparaben, wherein:
    the amount of dioxidine is about 0.1 to about 10 wt % based on the total weight of the composition;
    the amount of poviargol is about 0.1 to about 10 wt % based on the total weight of the composition;
    the amount of benzalkonium chloride is about 0.01 to about 2 wt % based on the total weight of the composition;
    the amount of methylparaben is about 0.001 to about 2 wt % based on the total weight of the composition; and
    the amount of propylparaben is about 0.001 to about 2 wt % based on the total weight of the composition.

2. The composition of claim 1, wherein the amount of PVP is about 5 to about 10 wt % based on the total weight of the composition.

3. The composition according to claim 1, wherein the molecular weight of the PVP is about 2,000,000 Da.

4. The composition according to claim 1, wherein the amount of unithiol is about 0.1 to about 10 wt % based on the total weight of the composition.

5. The composition according to claim 1, wherein the amount of dimethylsulfoxide is about 0.05 to about 5 wt % based on the total weight of the composition.

6. The composition according to claim 1, wherein one or more anesthetics are one or more local anesthetics.

7. The composition of claim 6, wherein one or more of the anesthetics are lidocaine, trimecaine, tetracaine, novocaine or a combination thereof.

8. The composition according to claim 1, wherein the amount of one or more anesthetics is about 0.01 to about 10 wt % based on the total weight of the composition.

9. The composition according to claim 1, additionally comprising an aqueous carrier.

10. The composition of claim 1, wherein said one or more antiseptics are selected from the group consisting of dioxidine, benzalkonium chloride, poviargol, methylparaben, propylparaben, and combinations thereof.

11. The composition according to claim 1, wherein the amount of one or more antiseptics is about 0.01 to about 20 wt % based on the total weight of the composition.

12. The composition according to claim 1, additionally comprising auxiliary components selected from the group consisting of pharmaceutical agents, wetting agents, surfactants, viscosity modifiers, stabilizers, substances promoting tissue regeneration and growth, cytokines, vitamin K, fibrinogen, thrombin, factor VII, factor VIII, colorants and flavoring agents.

13. The composition of claim 12, wherein said auxiliary components are present in the composition in an amount of 20 wt % or less.

14. The composition according to claim 1 for use in wound treatment.

15. A method of using the composition according to claim 1 as an agent for wound treatment, comprising applying said composition to a wound surface.

16. A method for treating a wound using an antiseptic composition according to claim 1, comprising applying said composition to a wound surface.

17. The method of claim 16, wherein the composition is further fixed on the wound surface using a sterile gauze dressing.

* * * * *